United States Patent [19]

Sperry, III

[11] 4,427,945

[45] Jan. 24, 1984

[54] MOLDED CONDUCTIVITY CELL BODY

[75] Inventor: Elmer A. Sperry, III, Pompton Plains, N.J.

[73] Assignee: Beckman Instruments, Inc., Fullerton, Calif.

[21] Appl. No.: 437,401

[22] Filed: Oct. 28, 1982

[51] Int. Cl.³ .............................................. G01N 27/02
[52] U.S. Cl. ..................................... 324/446; 324/441
[58] Field of Search ............................... 324/441, 446

[56] References Cited

U.S. PATENT DOCUMENTS

| | | | |
|---|---|---|---|
| 1,592,979 | 7/1926 | Keeler | 324/446 |
| 1,670,640 | 5/1928 | Smith | 324/446 |
| 3,551,802 | 12/1970 | Kuczynski | 324/446 |
| 3,774,104 | 11/1973 | Andersen | 324/441 |

Primary Examiner—Howard S. Williams
Assistant Examiner—Terryence Chapman

Attorney, Agent, or Firm—R. J. Steinmeyer; P. R. Harder; E. C. Jason

[57] ABSTRACT

A molded one-piece housing for use in fabricating conductivity cells. An electrically nonconducting housing includes an internal partition which divides the interior of the housing into a first region for receiving a test liquid and a second region for receiving a plurality of electrical conductors. Openings through the partition provide passages through which measuring electrodes may project into the first region to establish cell constants of the desired magnitude. These openings are so shaped that they establish a liquid-tight seal between the housing and the electrodes during insertion. By means of this seal the electrodes are held firmly in place during the assembly of the cell. This seal also permits a potting compound to be introduced into the second region without leaking onto and thereby affecting the electrical characteristics of the electrodes.

13 Claims, 11 Drawing Figures

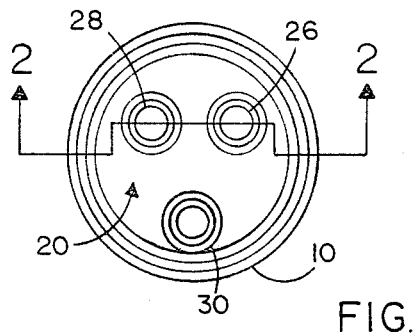
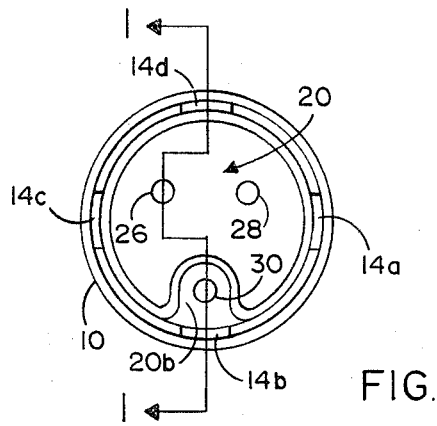
FIG. 1a    FIG. 1b
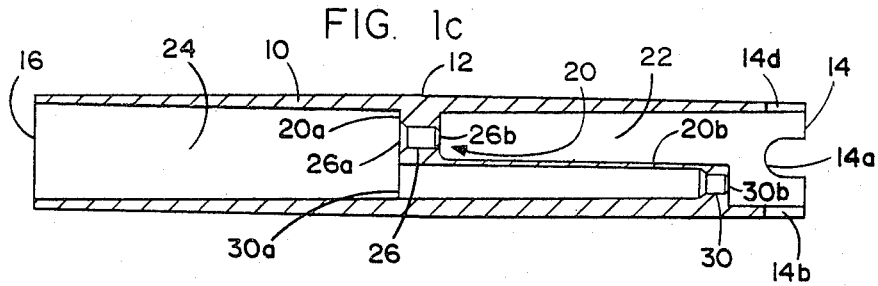
FIG. 1c
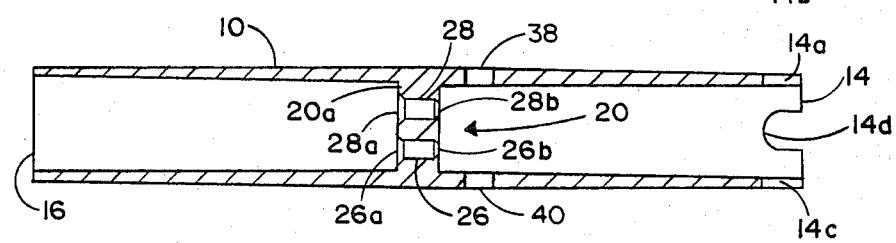
FIG. 1d
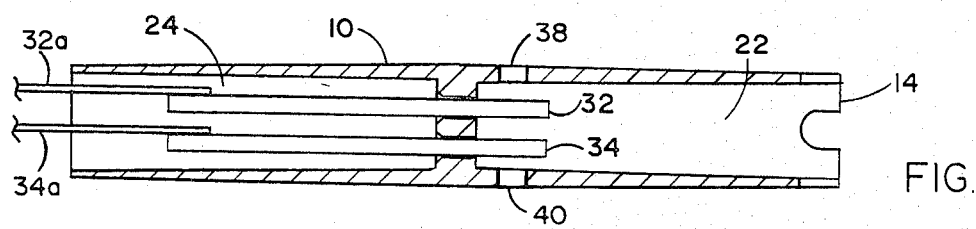
FIG. 2a
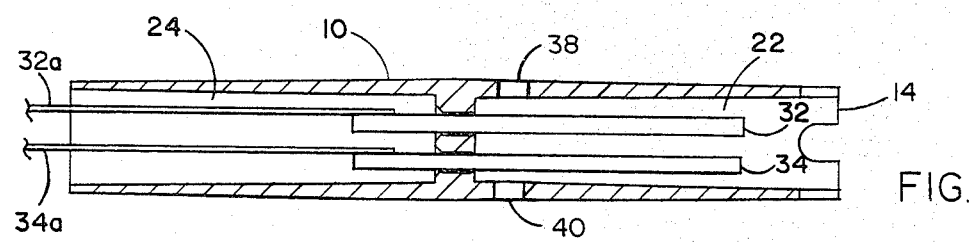
FIG. 2b

MOLDED CONDUCTIVITY CELL BODY

BACKGROUND OF THE INVENTION

Because useful information concerning the composition of a liquid can be derived by measuring its conductivity, conductivity measuring cells have come into widespread use as analytical tools. Conductivity cells include a pair of electrodes for immersion in a body of liquid of known size and shape, and are used by applying a known voltage and measuring the resulting current. Equivalently, a known current may be established between the electrodes and the resulting voltage measured.

Because test liquids may have a wide range of conductivities, it is customary to use a conductivity cell with an electrode length and spacing that is appropriate for the expected range of conductivity for the liquid. In liquids that have high resistances (i.e., low conductivities), for example, it is desirable to have the electrodes project deeply into the solution so that the flow of current therebetween has a conveniently measurable magnitude. With liquids that have low resistances (i.e., high conductivities), on the other hand, it is desirable to have the electrodes project less deeply into the solution so that the flow of current therebetween again has a conveniently measurable magnitude. A conductivity cell of the former type is said to have a low cell constant, while a cell of the latter type is said to have a high cell constant.

While the possibility of making the cell constant adjustable by providing an adjustable electrode length would appear to be attractive, it is not in many cases economical or convenient to do so. One reason is that the conductivity of a liquid is a nonlinear function of the exposed electrode length due to fringing and other effects. This nonlinearity makes it necessary either to provide an adjustment arrangement which takes into account this nonlinearity, or to restandardize the cell after each change in electrode length. As a practical matter, therefore, it is more economical and convenient to have a number of conductivity cells with different fixed cell constants and to change cells when liquids having different ranges of conductivity are to be measured.

While the above-described way of dealing with the need for differing cell constants simplifies the task of the cell user, it complicates the task of the cell manufacturer. The reason is that, prior to the present invention, manufacturers have been able to mount electrodes in cell housings in one of two basic ways. Firstly, the manufacturer could premold the electrodes into a molded subassembly that provided the desired electrode length and/or spacing and then mount this subassembly into a cell housing of a common, standard design. This approach is relatively costly because it involves the cost of producing a number of different molds and molded subassemblies for the different electrode configurations, and the cost of the structures and parts necessary to align and retain the different electrode subassemblies within the cell housing. Secondly, the manufacturer could mold a number of different cell housings in which electrodes could be potted to provide the desired cell constants. This approach is also relatively costly because of the investment necessary to produce the molds for a number of different housings. In addition, the potting compound often leaked onto or wetted parts of the electrodes that must be bare metal, causing the cell constant the deviate from the desired value.

SUMMARY OF THE INVENTION

In accordance with the present invention, there is provided a molded conductivity cell housing which eliminates both the need for molded electrode subassemblies, and the expense and difficulties associated with the potting of electrodes within different types of cell housings. In particular, the present invention contemplates a single piece molded conductivity cell housing which is adapted to directly receive and retain electrodes and which can provide a wide range of cell constants. With the use of the cell housing of the invention, the cost and difficulty of manufacturing conductivity cells having a wide range of cell constants are both significantly reduced.

In the preferred embodiment the conductivity cell housing of the invention includes an outer shell having a first open end for immersion in a test liquid and a second open end through which the electrodes may be inserted. The interior of the housing is provided with a partition, preferably integral with the outer shell, which divides the interior of the shell into a first region that is to be open to the test solution and a second region in which the electrodes may be connected to a cable that leads to a remote instrument console. A plurality of openings are provided through the partition so that electrodes may be pushed through to make contact with the test liquid. The composition of the housing and the shape of the openings are so selected that they automatically form a deformable liquid-tight seal with the electrodes as the latter are pushed therethrough. Once the electrodes have been pushed through these openings to the distance necessary to establish the desired cell constants, the above seals hold the electrodes firmly in position while the second region is sealed with a suitable potting compound. During the latter process, the seals assure that the potting compound cannot run down onto the electrodes and thereby change the desired cell constant.

In the preferred embodiment the partition is provided with one or more alternative openings, the use of which makes available a range of cell constants which cannot be achieved with only two openings. During assembly, any unused openings are simply blocked off with suitable inserts before the second region of the housing is potted. Because these additional openings may be located on a portion of the partition that projects into the first region of the cell, a particularly wide range of cell constants is made possible.

In another embodiment of the invention the partition is so shaped that it establishes a cavity within which temperature sensing thermistors may be mounted in the immediate vicinity of the electrodes. These thermistors constantly monitor the temperature of the solution during the measurement so that the measured conductivity value may be corrected for temperature effects on a real time basis. Significantly, this feature may be provided without surrendering either the above-mentioned integral construction or the ability to provide a wide range of cell constants.

DESCRIPTION OF THE DRAWINGS

Other objects and advantages of the present invention will be apparent from the following drawings in which:

FIGS. 1a and b are end views of the preferred embodiment of the conductivity cell housing of the invention, FIG. 1c is a cross-sectional view based on section line 1—1 of FIG. 1b, FIG. 1d is a cross-sectional view based on section line 2—2 of FIG. 1a, FIGS. 2a–d are cross-sectional views of the housing of FIG. 1 that show the electrode positions that are associated with differing cell constants, FIGS. 3a and b are end and cross-sectional views of another embodiment of a conductivity cell housing constructed in accordance with the invention.

DESCRIPTION OF THE PREFERRED EMBODIMENTS

Figure 2C:
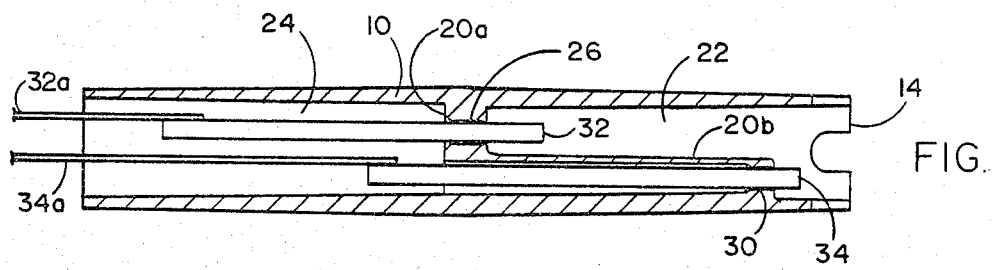

Referring to FIGS. 1a–d there are shown two end and two cross-sectional views of the preferred embodiment of the conductivity cell housing of the invention. Generally speaking, this cell housing includes a molded one-piece outer shell 10 which is preferably, although not necessarily, cylindrical in shape. A slight taper is provided on both the inner and outer surfaces of the shell 10 to facilitate its withdrawal from its mold. The parting line for these tapered surfaces is preferably at or near the middle of the housing, as indicated by the number 12 in FIG. 1c. Housing 10 may in general be composed of any chemically inert thermoplastic material which is electrically nonconducting such as, for example, polysulfone plastics, polyvinyl chloride, and polyester plastics, among others. Housing 10 is, however, preferably composed of plastics such as polysulfones which will deform slightly under pressure without cracking.

The first or front end 14 of the housing is open so that the liquid to be measured may enter the interior of the housing and make contact with the electrodes that will be mounted therein. The circulation of the test fluid through the housing is facilitated by providing cutaway sections which in the present embodiment include four generally half-circular channels 14a–d, which may be seen together in FIG. 1b. The movement of the test fluid into the interior of the housing is also facilitated by providing holes through shell 10 at suitable locations (see 38 and 40 in FIG. 1d), so that air may escape and solution circulate.

The second or rear end of the housing 16 is also open and is adapted to receive an electrical cable having conductors for connection to the electrodes of the cell. These conductors are preferably soldered to the electrodes before the latter are pushed into place and potted within the housing. Once this has been done, the space between the cable conductors and the open end of the housing may be closed with a conventional rubber end cap or boot (not shown).

Figure 3B:
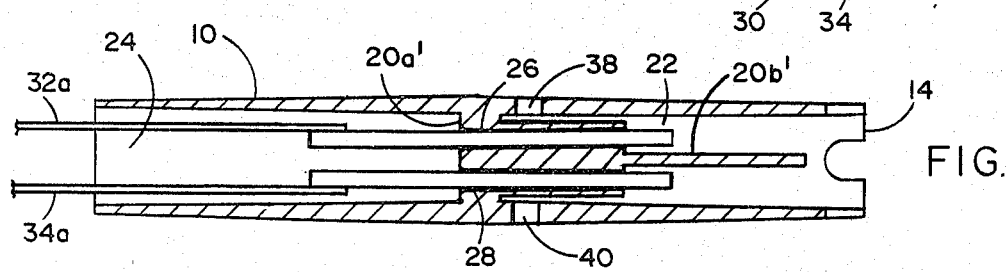

In accordance with an important feature of the present invention, the interior of the housing is provided with a partition 20 which divides that interior into a first region 22 which extends toward first end 14 and a second region 24 which extends toward second end 16. In the preferred embodiment, partition 20 includes a base section 20a and an elongated section 20b which projects into region 22. While elongated section 20b is shown as being located adjacent to shell 10, it may in general be located at any of a number of different positions within shell 10 as shown in FIG. 3b.

Internal partition 20 includes a plurality of openings 26, 28 and 30 through which electrodes may be pushed during the assembly of the cell. In the embodiment of FIG. 1, two of these openings 26 and 28 are located in base section 20a of partition 20 and opening 30 is located in elongated section 20b thereof. During assembly, electrodes may be pushed through any two of these three openings so that they project into housing region 22 where they will later make contact with the test solution.

As can be seen in FIGS. 1a, c, and d, each of openings 26–30 has an entrance end that is larger than its exit end. The entrance ends of these openings, designated by the postscript "a", have diameters that are preferably slightly larger than the diameters of the electrodes, and are provided with tapers to facilitate the entry of the electrodes. The smaller or exit ends of these openings, designated by the letter "b", each have a raised interior rim which gives way to an exit hole having a diameter slightly smaller than the diameter of the electrode to be pushed therethrough. This rim is preferably provided with a taper which facilitate the alignment of the electrodes with the exit hole.

The fact that the diameter of the exit hole of each opening is slightly smaller than the diameter of the electrode to be pushed therethrough assures that, as the electrodes are pushed through respective openings, the raised interior rim is deformed. The force of compression that is associated with this deformation serves to establish a substantially fluid-tight seal between the electrode and the cell housing. This seal is desirable since it allows housing region 24 to later be filled with potting compound without allowing the latter to leak through the openings and alter the electrical characteristics of the electrodes. This force of compression also assures that the electrodes stop and remain in position as soon as the force which pushes them through these openings is removed. As a result, the electrodes may be stopped at any of a virtually unlimited number of different positions within the housing, each position being associated with a respective cell constant.

If, for example, as shown in FIG. 2a, the ends of electrodes such as 32 and 34, with their respective conductors 32a and 34a attached, are driven only a short distance into region 22, the resulting conductivity cell will have a relatively high cell constant. If, on the other hand, as shown in FIG. 2b, the ends of electrodes 32 and 34 are driven relatively far into region 22, the resulting conductivity cell will have a relatively low cell constant. Notwithstanding the depth to which electrodes 32 and 34 are driven into region 22, however, the electrodes will stop and be held firmly in place at the position that they occupied when the driving force was removed. Thus, by controlling the depth to which the electrodes are inserted, a wide range of different cell constants may be produced.

Figure 2D:
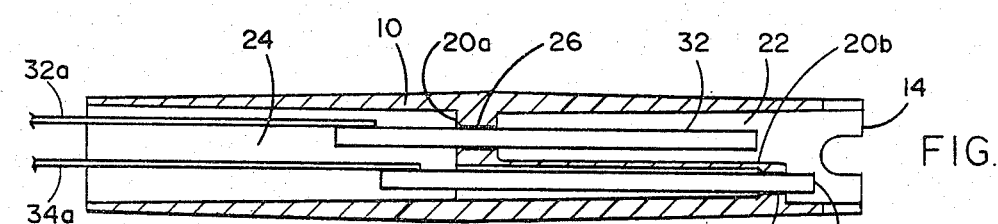

Referring to FIG. 2c there is shown an embodiment of the invention which makes use of opening 30 of elongated section 20b and opening 26 of base section 20a of partition 20. Because of the increased length of the path between electrodes 32 and 34 in this configuration, the conductivity cell shown in FIG. 2c will have a cell constant which is substantially higher than that which is available from the cell-electrode configurations shown in FIGS. 2a and b. Naturally, as electrode 32 of FIG. 2c is driven more deeply into region 22, as shown in FIG. 2d, the cell constant will approach the cell constant of the cell shown in FIG. 2a. If the insertion depth is increased still further, a condition will be reached in which the cell constant of the cell of FIG. 2d will be equal to or even less than that of FIG. 2a. It will therefore be seen that, by making use of elongated section 20b of partition 20, it is possible to use the housing of the invention to produce cells having any cell constant that lies between the cell constant of the cell shown in FIG. 2c and that of the cell shown in FIG. 2b.

As a specific example, by using the housing of the invention, it has been possible to produce cells having a cell constant as low as 0.1/centimeter and as high as 2.16/centimeter, i.e., a factor of more than 20. Moreover, because either electrode can be stopped at any desired position in either opening, it is possible to produce any desired cell constant between the abovementioned extremes. This ability is highly desirable since it makes possible the manufacture of conductivity cells having special (non-standard) cell constants without requiring special cell housings, electrodes or assembly equipment.

Figure 3A:
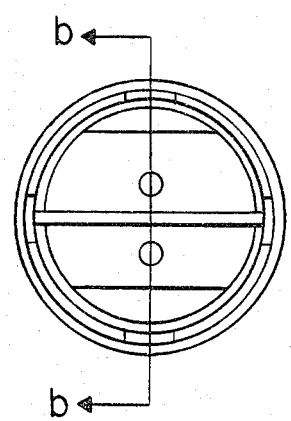

Referring to FIGS. 3a and b, there are shown end and cross-sectional views of an embodiment of the invention which provides a range of cell constants which is even greater than that available from the embodiment of FIG. 1. The embodiment of FIG. 3 is generally similar to that of FIG. 1, like functioning parts being similarly numbered. One difference between the embodiment of FIG. 3 and that of FIG. 1 is that in FIG. 3 the elongated section 20b' of the partition is located between openings 26 and 28 rather than to one side thereof. This location for the elongated section enables it to serve as separator to in effect subdivide first region 22 into a first subregion surrounding electrode 32 and a second subregion surrounding electrode 34. The advantage of this subdivision is that it increases the length of the path between the electrodes. In addition, the cross-sectional area of this path is reduced. It is therefore possible for the embodiment of FIG. 3 to have a cell constant that is on the order of twenty times as high as that of the embodiment shown in FIG. 2c. On the other hand, when electrodes 32 and 34 are driven deeply enough into region 22 that they extend near or even beyond the end of elongated section 20b', the cell constant of the resulting cell will be comparable to that associated with the cell of FIG. 2a.

Another difference between the embodiment of FIG. 3 and that of FIG. 1 is that base section 20a' is so shaped that the electrodes emerge therefrom in a position that is forward of holes 38 and 40. The spacing between the electrodes and holes 38 and 40 is desirable because it tends to reduce the cell constant lowering effect of holes 38 and 40.

Figure 4:
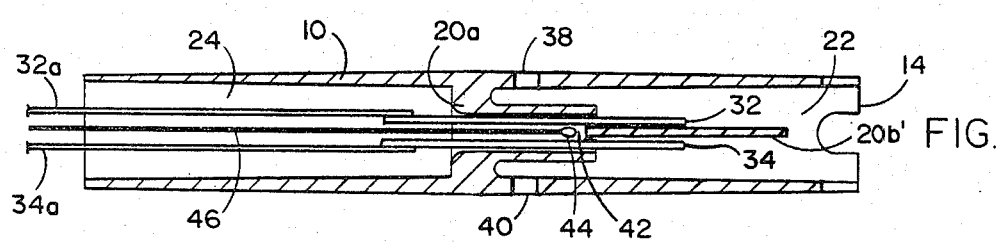
FIG. 4 is a cross-sectional view of still another embodiment of the present invention.

Referring to FIG. 4, there is shown a cross-sectional view of still another embodiment of the present invention. The embodiment of FIG. 4 is generally similar to that of FIGS. 1 and 3, like functioning parts being similarly numbered. The embodiment of FIG. 4 differs from that of FIG. 3 primarily in that base section 20a' includes a cavity 42 which will in use be substantially surrounded by the liquid within region 22. Cavity 42 is desirable because it serves as an ideal location for a temperature sensing thermistor such as 44 which may be connected to the external cable through a conductor pair 46. From cavity 42 thermistor 44 will provide to the external conductivity measuring instrument a temperature-dependent signal indicative of the temperature in the immediate vicinity of electrodes 32 and 34. By means of this signal, the external instrument can correct its conductivity readings in a known manner to eliminate temperature-related measurement errors.

In view of the foregoing, it will be seen that the conductivity cell housings of the invention comprises an extremely inexpensive single-piece structure which makes possible the fabrication of conductivity cells having a wide range of cell constants. In addition, the housing of the invention facilitates the assembly of the conductivity cell by providing openings which clamp the electrodes in any desired position while the cell is being potted. These openings also serve as a deformable liquid-tight seal to prevent the potting compound from leaking onto the electrodes and thereby affecting the cell constant established thereby.

What is claimed is:

1. A molded housing for a conductivity cell comprising:
   (a) a shell having a first open end for immersion in a test solution, and a second open end for receiving a plurality of electrical conductors,
   (b) a partition, integral with said shell, for dividing the interior of the shell into a first region in the vicinity of the first open end and a second region in the vicinity of the second open end
   (c) a plurality of openings through said partition for receiving and retaining a plurality of respective electrodes
   (d) said housing being composed of an electrically nonconductive material which deforms slightly to establish liquid tight seals between the electrodes and the partition as said electrodes are pushed through respective openings.

2. The housing of claim 1 in which the material is selected from the group consisting of polysulfone, polyvinyl chloride and polyester plastics.

3. The housing of claim 1 in which each of said openings includes an exit end having a diameter which is less than the diameter of the electrode to be pushed therethrough.

4. The housing of claim 1 in which each of said openings includes a raised interior rim which deforms as an electrode is pushed therethrough.

5. The housing of claim 1 in which the partition includes an elongated section that extends in the direction of said first end and provides a path of increased length between said openings.

6. The housing of claim 5 in which said elongated section is adjacent to the inner surface of said shell.

7. The housing of claim 5 in which said elongated section divides said first region into a plurality of subregions.

8. The housing of claim 5 in which the elongated section includes at least one of said openings.

9. The housing of claim 1 in which the partition includes a base section that is generally perpendicular to the longitudinal axis of the shell and an elongated section that is generally parallel to that longitudinal axis.

10. A housing as set forth in claim 1 which is adapted to provide cell constants which differ by a factor of at least twenty.

11. A conductivity cell comprising:
   (a) a shell having a first end for immersion in a test solution, and a second end for receiving a plurality of electrical conductors,
   (b) a partition, integral with said shell, for dividing the interior thereof into a first region open to said first end and a second region open to said second end, (c) at least two electrodes, (d) a plurality of openings in said partition through which respective electrodes may project from the first region into the second region, each of said openings including means for establishing a seal with an electrode when the latter is pushed therethrough, (e) the cell constant of said cell being selectable by selecting the distance that the electrodes are pushed through respective openings.

12. The housing of claim 11 in which the seal establishing means comprises a deformable circumferential ridge on the interior of each opening.

13. The housing of claim 11 in which the cell constants which may be established by causing the electrodes to project differing distances into the second region differ by a factor of at least twenty.

* * * * *